US008920473B2

(12) United States Patent
Trautwein et al.

(10) Patent No.: US 8,920,473 B2
(45) Date of Patent: Dec. 30, 2014

(54) POSTERIOR FUNCTIONALLY DYNAMIC STABILIZATION SYSTEM

(75) Inventors: Frank T. Trautwein, Filderstadt (DE); Bernhard Holtkamp, Donaueschingen (DE); Rudolf Bertagnoli, Vienna (AT); Markus Salvermoser, Möhringen (DE); Gary L. Lowery, Jacksonville, FL (US); Guntmar H. Eisen, Tuttlingen (DE)

(73) Assignee: Paradigm Spine, LLC, New York, NY (US)

(*) Notice: Subject to any disclaimer, the term of this patent is extended or adjusted under 35 U.S.C. 154(b) by 933 days.

(21) Appl. No.: 11/952,575

(22) Filed: Dec. 7, 2007

(65) Prior Publication Data
US 2008/0312693 A1 Dec. 18, 2008

Related U.S. Application Data

(60) Provisional application No. 60/869,342, filed on Dec. 10, 2006, provisional application No. 60/914,360, filed on Apr. 27, 2007.

(51) Int. Cl.
*A61B 17/70* (2006.01)
*A61B 17/17* (2006.01)
*A61B 17/88* (2006.01)
*A61B 19/00* (2006.01)

(52) U.S. Cl.
CPC ......... *A61B 17/7023* (2013.01); *A61B 17/7025* (2013.01); *A61B 17/8897* (2013.01); *A61B 2019/307* (2013.01); *A61B 17/1757* (2013.01); *A61B 2019/461* (2013.01); *A61B 17/8863* (2013.01); *A61B 17/7007* (2013.01); *A61B 17/708* (2013.01)
USPC .............................. 606/257; 606/246; 606/259

(58) Field of Classification Search
USPC ........... 606/61, 246, 279, 300–321, 247–249, 606/250–275
See application file for complete search history.

(56) References Cited

U.S. PATENT DOCUMENTS

| | | |
|---|---|---|
| 1,509,715 A | 9/1924 | Dacar |
| 4,570,618 A | 2/1986 | Wu |

(Continued)

FOREIGN PATENT DOCUMENTS

| | | |
|---|---|---|
| EP | 0 677 277 A2 | 10/1995 |
| EP | 0 919 199 A2 | 6/1999 |

(Continued)

OTHER PUBLICATIONS

International Search Report for International Application No. PCT/US2007/086800 mailed May 20, 2008.

(Continued)

*Primary Examiner* — Mary Hoffman
*Assistant Examiner* — Christina Negrellirodrigue
(74) *Attorney, Agent, or Firm* — MH2 Technology Law Group, LLP

(57) ABSTRACT

A functionally dynamic stabilization unit and system for treatment of spinal instability are provided. Each unit, and collectively, the system, is configured to control flexion, extension and translation of the affected unstable vertebral area, thereby stabilizing the vertebral segments by restoring normal function. This is achieved by providing a unit and system that allow for lateral bending, axial compression, rotation, anterior segmental height adjustment, and posterior segmental height adjustment. The unit and system provide sufficient segmental stiffness, while also limiting, or controlling, the range of motion (i.e., sufficient stiffness in the neutral or active zone, while limiting or preventing motion outside of the active zone) to stabilize the vertebral segments. In use, the system mimics the natural movement of the normal spine. Furthermore, the system includes a rigid, fusion-promoting coupler configured for use in an adjacent level, or as a substitute for the functionally dynamic unit. The modularity of the system allows adjustment over time and easier revision surgery, and is configured for minimally-invasive, delivery or implantation.

26 Claims, 17 Drawing Sheets

(56) References Cited

U.S. PATENT DOCUMENTS

| | | | |
|---|---|---|---|
| 4,604,995 | A | 8/1986 | Stephens et al. |
| 4,653,481 | A | 3/1987 | Howland et al. |
| 4,743,260 | A | 5/1988 | Burton |
| 4,815,453 | A | 3/1989 | Cortrel |
| 5,030,220 | A | 7/1991 | Howland |
| 5,375,823 | A | 12/1994 | Navas |
| 5,520,687 | A | 5/1996 | Howland |
| 5,540,688 | A | 7/1996 | Navas |
| 5,545,166 | A | 8/1996 | Howland |
| 5,672,175 | A | 9/1997 | Martin |
| 5,693,053 | A | 12/1997 | Estes |
| 5,733,284 | A | 3/1998 | Martin |
| RE36,221 | E | 6/1999 | Breard et al. |
| 5,961,516 | A | 10/1999 | Graf |
| 6,241,730 | B1 * | 6/2001 | Alby ............................ 606/256 |
| 6,248,106 | B1 | 6/2001 | Ferree |
| 6,267,764 | B1 | 7/2001 | Elberg |
| 6,273,914 | B1 | 8/2001 | Papas |
| 6,296,644 | B1 | 10/2001 | Saurat et al. |
| 6,440,189 | B1 | 8/2002 | Sugano et al. |
| 6,616,669 | B2 | 9/2003 | Ogilvie et al. |
| 6,875,212 | B2 | 4/2005 | Shaolian et al. |
| 6,899,713 | B2 | 5/2005 | Shaolian et al. |
| 7,811,309 | B2 * | 10/2010 | Timm et al. .................. 606/257 |
| 7,942,905 | B2 * | 5/2011 | Lim et al. ...................... 606/257 |
| 2002/0087159 | A1 | 7/2002 | Thomas |
| 2002/0133155 | A1 | 9/2002 | Ferree |
| 2002/0151978 | A1 | 10/2002 | Zacouto et al. |
| 2002/0198526 | A1 | 12/2002 | Shaolian et al. |
| 2003/0055427 | A1 | 3/2003 | Graf |
| 2003/0171749 | A1 | 9/2003 | Le Couedic et al. |
| 2003/0191470 | A1 | 10/2003 | Ritland |
| 2003/0220642 | A1 | 11/2003 | Freudiger |
| 2003/0220643 | A1 | 11/2003 | Ferree |
| 2004/0002708 | A1 | 1/2004 | Ritland |
| 2004/0015167 | A1 | 1/2004 | Farkas et al. |
| 2004/0049189 | A1 | 3/2004 | Le Couedic et al. |
| 2004/0049190 | A1 | 3/2004 | Biedermann et al. |
| 2004/0082954 | A1 | 4/2004 | Teitelbaum et al. |
| 2004/0087950 | A1 | 5/2004 | Teitelbaum et al. |
| 2004/0092934 | A1 | 5/2004 | Howland |
| 2004/0116927 | A1 | 6/2004 | Graf |
| 2004/0138661 | A1 | 7/2004 | Bailey |
| 2004/0172025 | A1 | 9/2004 | Drewry et al. |
| 2004/0215193 | A1 | 10/2004 | Shaolian et al. |
| 2004/0236328 | A1 | 11/2004 | Paul et al. |
| 2004/0236329 | A1 | 11/2004 | Panjabi |
| 2004/0243127 | A1 | 12/2004 | Vincent-Prestigiacomo |
| 2004/0267260 | A1 | 12/2004 | Mack et al. |
| 2005/0038432 | A1 | 2/2005 | Shaolian et al. |
| 2005/0056979 | A1 * | 3/2005 | Studer et al. .................. 267/118 |
| 2005/0065514 | A1 * | 3/2005 | Studer ............................ 606/61 |
| 2005/0065515 | A1 | 3/2005 | Jahng |
| 2005/0065516 | A1 | 3/2005 | Jahng |
| 2005/0085815 | A1 | 4/2005 | Harms et al. |
| 2005/0113927 | A1 | 5/2005 | Malek |
| 2005/0124991 | A1 | 6/2005 | Jahng |
| 2005/0131407 | A1 | 6/2005 | Sicvol et al. |
| 2005/0143737 | A1 | 6/2005 | Pafford et al. |
| 2005/0149020 | A1 | 7/2005 | Jahng |
| 2005/0154390 | A1 | 7/2005 | Biedermann et al. |
| 2005/0165396 | A1 | 7/2005 | Fortin et al. |
| 2005/0171543 | A1 | 8/2005 | Timm et al. |
| 2005/0177156 | A1 | 8/2005 | Timm et al. |
| 2005/0177157 | A1 | 8/2005 | Jahng |
| 2005/0177164 | A1 | 8/2005 | Walters et al. |
| 2005/0177166 | A1 | 8/2005 | Timm et al. |
| 2005/0182400 | A1 | 8/2005 | White |
| 2005/0182401 | A1 | 8/2005 | Timm et al. |
| 2005/0182409 | A1 | 8/2005 | Callahan et al. |
| 2005/0203513 | A1 | 9/2005 | Jahng et al. |
| 2005/0203514 | A1 | 9/2005 | Jahng et al. |
| 2005/0203517 | A1 | 9/2005 | Jahng et al. |
| 2005/0203518 | A1 | 9/2005 | Biedermann et al. |
| 2005/0203519 | A1 | 9/2005 | Harms et al. |
| 2005/0222569 | A1 | 10/2005 | Panjabi |
| 2005/0228380 | A1 | 10/2005 | Moore et al. |
| 2005/0234451 | A1 | 10/2005 | Markworth |
| 2006/0025770 | A1 | 2/2006 | Schlapfer et al. |
| 2006/0189983 | A1 | 8/2006 | Fallin et al. |
| 2006/0189984 | A1 * | 8/2006 | Fallin et al. ..................... 606/61 |
| 2010/0087862 | A1 * | 4/2010 | Biedermann et al. ......... 606/259 |

FOREIGN PATENT DOCUMENTS

| | | |
|---|---|---|
| EP | 1 072 228 A1 | 1/2001 |
| WO | WO 01/45576 A1 | 6/2001 |
| WO | WO 01/56489 A1 | 8/2001 |
| WO | WO 02/067793 A2 | 9/2002 |
| WO | WO 02/085217 A2 | 10/2002 |
| WO | WO 02/102259 A2 | 12/2002 |
| WO | WO 03/047441 A1 | 6/2003 |
| WO | WO 03/047442 A1 | 6/2003 |
| WO | WO 2004/024011 A1 | 3/2004 |
| WO | WO 2005/030029 A2 | 4/2005 |
| WO | WO 2005/065375 A2 | 7/2005 |
| WO | WO 2006/045091 A2 | 4/2006 |
| WO | WO 2006/045091 A3 | 4/2006 |

OTHER PUBLICATIONS

Written Opinion of the International Searching Authority for International Application No. PCT/US2007/086800 mailed May 20, 2008.

International Search Report and Written Opinion for International Application No. PCT/US2007/086800 mailed Nov. 26, 2008.

Office Action for corresponding Mexican Application No. MX/a/2008/004558 received on Mar. 8, 2013.

Japanese Office Action for corresponding Appl. No. JP2009-541493 dated Aug. 14, 2012.

* cited by examiner

POSTERIOR FUNCTIONALLY DYNAMIC STABILIZATION SYSTEM

This application claims priority to U.S. Provisional Patent Application No. 60/869,342, which was filed on Dec. 10, 2006, and U.S. Provisional Patent Application No. 60/914,360, which was filed on Apr. 27, 2007, both of which are herein incorporated by reference in their entirety.

FIELD

The present invention relates to devices and methods for treating spinal conditions, and specifically to spinal stabilization systems for controlling or restricting relative motion between vertebrae.

BACKGROUND

The spine includes a series of joints known as motion segment units. Each unit represents the smallest component of the spine that exhibits a kinematic behavior characteristic of the entire spine. The motion segment unit is capable of flexion, extension, lateral bending, and translation. The components of each motion segment unit include two adjacent vertebrae, the corresponding apophyseal joints, an intervertebral disc, and connecting ligamentous tissue, with each component of the motion segment unit contributing to the mechanical stability of the joint. For example, the intervertebral discs that separate adjacent vertebrae provide stiffness that helps to restrain relative motion of the vertebrae in flexion, extension, axial rotation, and lateral bending.

When the components of a motion segment unit move out of position or become damaged due to trauma, mechanical injury or disease, severe pain and further destabilizing injury to other components of the spine may result. In a patient with degenerative disc disease (DDD), a damaged disc may provide inadequate stiffness, which may result in excessive relative vertebral motion when the spine is under a given load, causing pain and further damage to the disc. Depending upon the severity of the structural changes that occur, treatment may include fusion, discectomy, and/or a laminectomy.

Current surgical treatments often involve fusion of unstable motion segment units with removal of adjacent tissue. For numerous reasons, fusion may be an undesirable treatment option. For instance, fusion results in a permanent, rigid fixation with irreversible loss of range of motion at fused vertebral levels. In addition, loss of mobility at the fused levels causes stress to be transferred to other neighboring motion segments, which can cause or accelerate degeneration of those segments. Moreover, fusion often does not alleviate some or all of the pain.

It would thus be desirable to provide a spinal stabilization system that is sufficiently functionally dynamic to manage the load sharing characteristics of the treated spine. It would further be desirable to provide a system that would allow close-to-normal motion, mimicking the physiological response of a healthy motion segment and providing pain relief.

SUMMARY

The present disclosure provides a functionally dynamic stabilization unit and system for treatment of spinal instability due to, for example, injury, trauma, or degenerative disc disease (DDD). Each unit, and collectively, the system, is configured to control flexion, extension, and translation of affected vertebrae, thereby stabilizing the vertebral segments by restoring normal function. This is achieved by providing a unit and system that allow for lateral bending, axial compression, rotation, anterior segmental height adjustment, and posterior segmental height adjustment. The unit and system provide sufficient segmental stiffness, while also controlling the range of motion to stabilize the vertebral segments. In use, the system mimics the natural movement of the normal spine. Furthermore, the system is configured to allow adjustment over time, revision surgery (e.g., fusion), and percutaneous implantation.

In accordance with one exemplary embodiment, a functionally dynamic spinal stabilization system is provided. The system may comprise a flexible coupler and can include a cylindrical body portion including one or more slots in the wall of the cylindrical body. The system can further include a pair of gripping arms for attachment to bone anchors, the arms being located at opposed ends of the coupler. The flexible coupler may also include an internal range-of-motion limiting mechanism configured to limit motion of the flexible coupler in bending, compression, and tension. The system can further comprise a pair of bone anchors configured to cooperate with the gripping arms for attachment to bone tissue.

In accordance with another exemplary embodiment, the system further includes a rigid coupler having a pair of gripping arms for attachment to bone anchors. Like the flexible coupler, the arms can be located at opposed ends of the coupler. However, unlike the flexible coupler, this coupler does not allow extension or compression. Rather, the coupler promotes fusion by preventing motion at this segment.

Also provided is a method of treating a spine. The method can comprise attaching a first bone anchor to a vertebra and attaching a second bone anchor to an adjacent vertebrae. A flexible coupler may then be attached to the first and second bone anchors. The flexible coupler can include a cylindrical body portion having one or more slots in the wall of the cylindrical body and an internal range-of-motion limiting mechanism configured to limit motion of the flexible coupler in bending, compression, and tension.

Also provided is a method of percutaneous implantation of the system that minimizes tissue damage and eases insertion, as well as an instrument set for performing this method. The method can include producing at least one incision over at least two adjacent vertebrae to be treated and positioning at least two wires such that each wire separately contacts a pedicle of one the at least two vertebrae. A screw may be secured to each vertebrae, and the distance between the screws inserted into two adjacent vertebrae is measured. A flexible coupler to be attached to the screws is selected, and the length of the flexible coupler is adjusted based on the distance measured.

It is to be understood that both the foregoing general description and the following detailed description are exemplary and explanatory only and are not restrictive of the disclosure, as claimed.

The accompanying drawings, which are incorporated in and constitute a part of this specification, illustrate several embodiments of the disclosure and together with the description, serve to explain the principles of the disclosure.

Additional objects and advantages of the disclosure will be set forth in part in the description which follows or may be learned by practice of the disclosure. The objects and advantages of the disclosure will be realized and attained by means of the elements and combinations particularly pointed out in the appended claims.

DESCRIPTION OF THE EMBODIMENTS

The present disclosure provides a functionally dynamic stabilization unit and a system incorporating functionally dynamic stabilization units for treatment of spinal instability. The present disclosure further provides minimally-invasive methods for implanting spinal stabilization systems, as well as instruments that will facilitate these methods.

The unit, system, and methods of the present disclosure may be used to treat spinal pathologies caused by, for example, injury, trauma, or degenerative disc disease (DDD). The stabilization unit and systems comprising such units are configured to control flexion, extension and translation of an affected unstable vertebral area, thereby stabilizing vertebral segments and restoring normal function. This is achieved by providing a unit and system that allow for lateral bending, axial compression, rotation, anterior segmental height adjustment, and posterior segmental height adjustment on the spine. The unit and system provide sufficient segmental stiffness within a patient's neutral or active zone, while also limiting or controlling range of motion outside a desired zone. In use, the system mimics the natural movement of the normal spine. Furthermore, the system is configured to allow adjustment over time, revision surgery, and percutaneous delivery or implantation.

Figure 1:
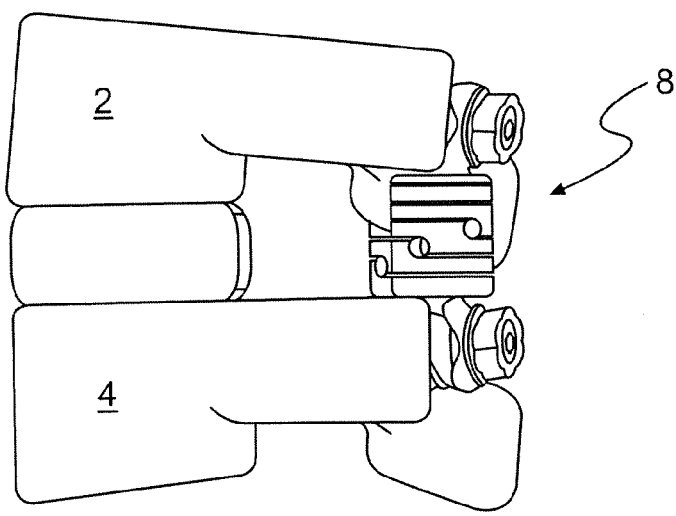
FIG. 1 illustrates a side perspective view of an implanted functionally dynamic stabilization system.
Figure 2:
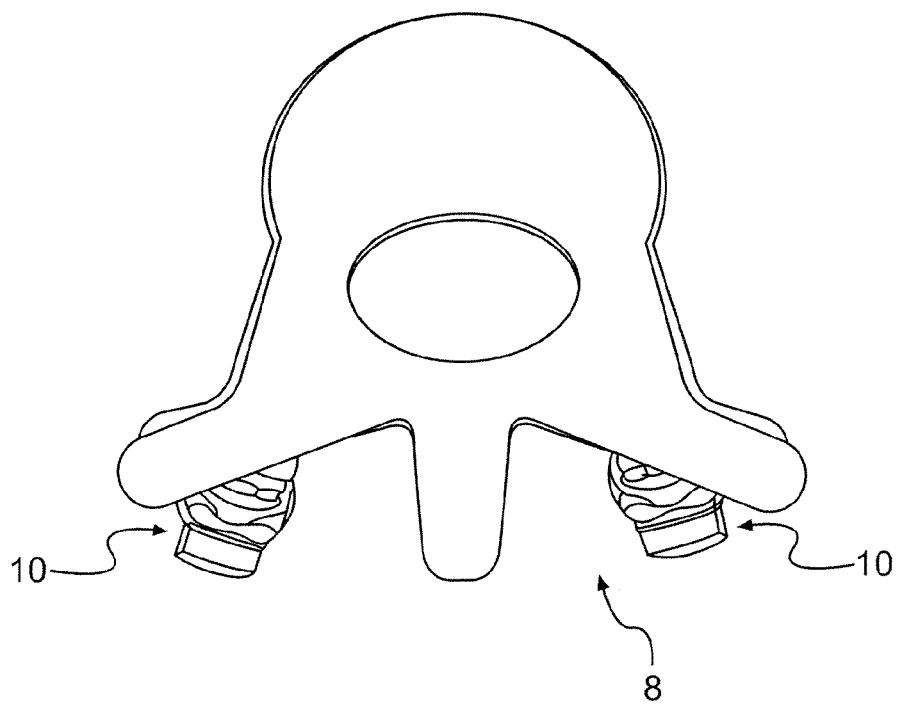
FIG. 2 illustrates a top view of the implanted functionally dynamic stabilization system of FIG. 1, including two stabilization units on opposite sides of the spine.
Figure 3:
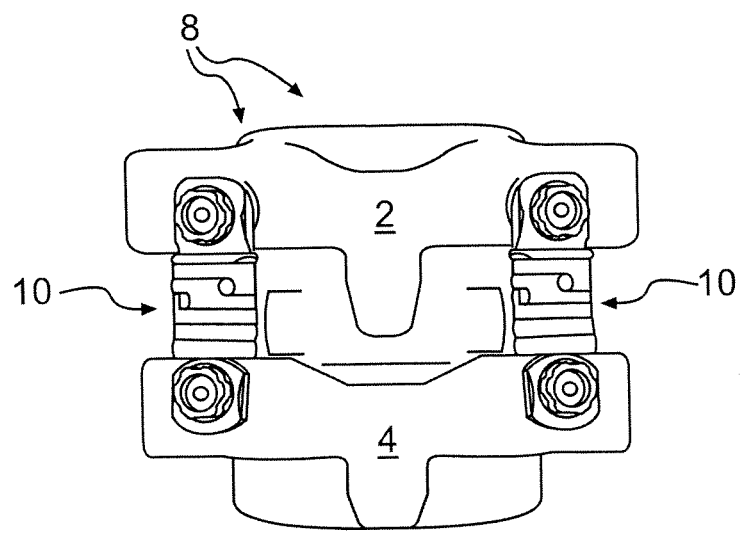
FIG. 3 illustrates a posterior view of the system of FIGS. 1-2.

Turning now to the drawings, FIG. 1 shows an embodiment of a functionally dynamic stabilization system 8, implanted between adjacent vertebrae 2, 4. FIG. 2 illustrates a top view of an implanted functionally dynamic stabilization system, and FIG. 3 illustrates a posterior view of the system 8 of FIGS. 1-2. As shown, the system 8 can include one or more flexible stabilization units 10 that can be implanted on a posterior portion of the spine to stabilize affected vertebrae 2, 4.

Figure 4A:
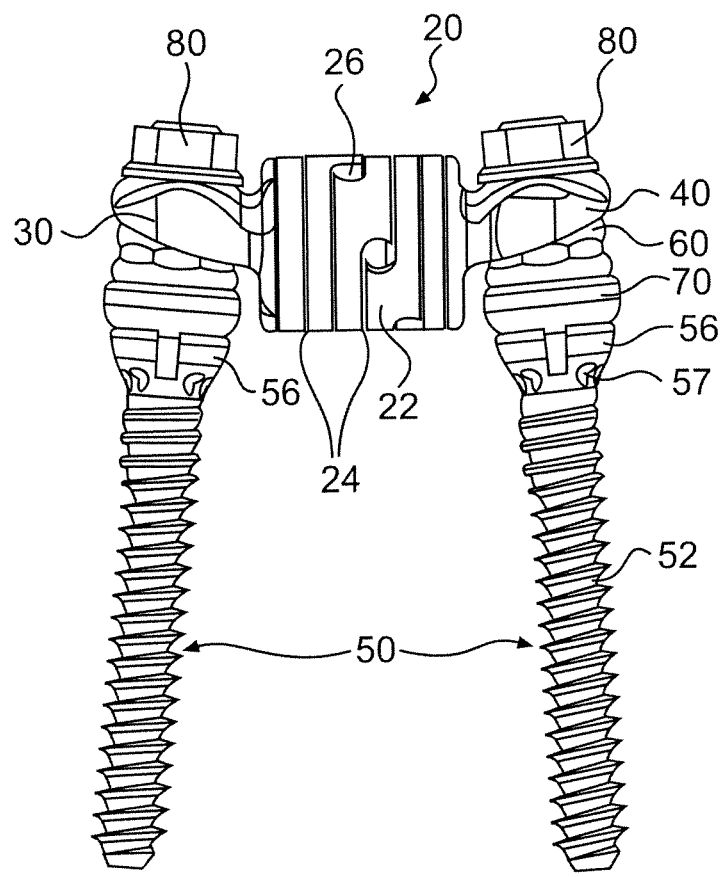
FIG. 4A illustrates a perspective view of one stabilization unit of the system of FIGS. 1-3.
Figure 4B:
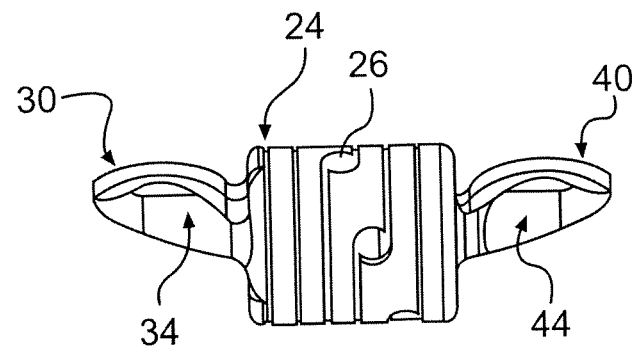
FIG. 4B illustrates a side view of a portion of a flexible coupler used in the stabilization unit of FIG. 4A.
Figure 4C:
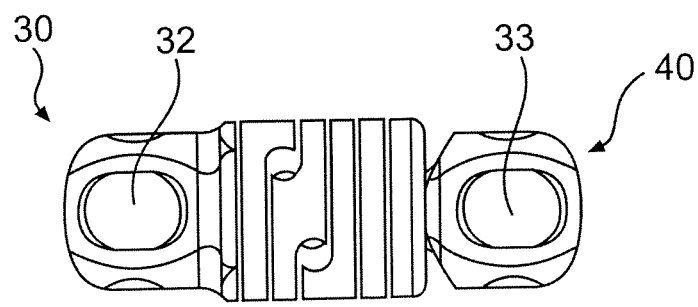
FIG. 4C illustrates a top view of the flexible coupler of FIG. 4B.

As shown in FIG. 4A, each functionally dynamic stabilization unit 10 may comprise a flexible coupler 20 connected to at least one bone anchor 50, such as a pedicle screw or bone screw. The coupler 20 may comprise a flexible body 22 including slots 24 and openings 26. As shown in FIGS. 4B-4C, the flexible body 22 may include, at one end, a gripping arm 30 having an opening 32 for insertion of a bone anchor 50, and at an opposite end a second gripping arm 40, also having an opening 33 for receiving a bone anchor 50. The gripping arms 30, 40 may be integrally formed with the body 22 or may be detachably connected to the body 22. For example, one end of the gripping arm 40 may be threaded for connection to the flexible body 22 via, for example, a sleeve 90 in the flexible body 22, as shown in FIG. 6.

Figure 5A:
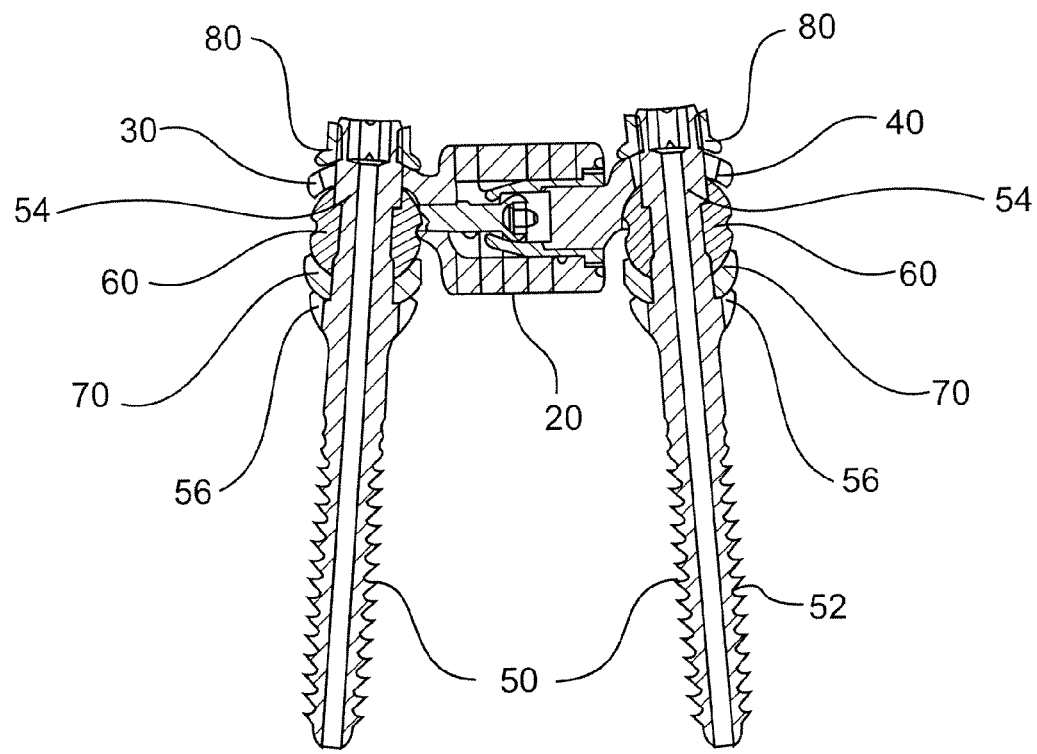
FIG. 5A illustrates a cross-sectional view of the unit of FIG. 4A.
Figure 5B:
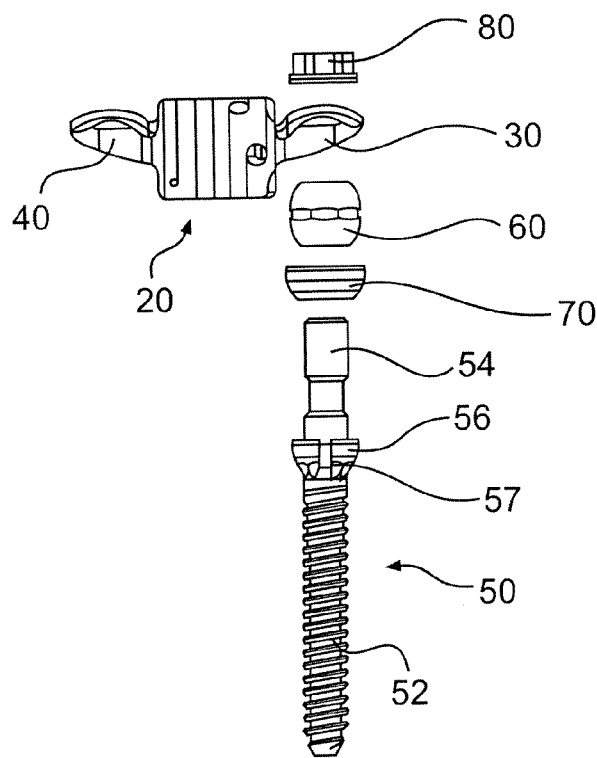
FIG. 5B illustrates an exploded view of a portion of the stabilization unit of FIG. 4A.
Figure 6:
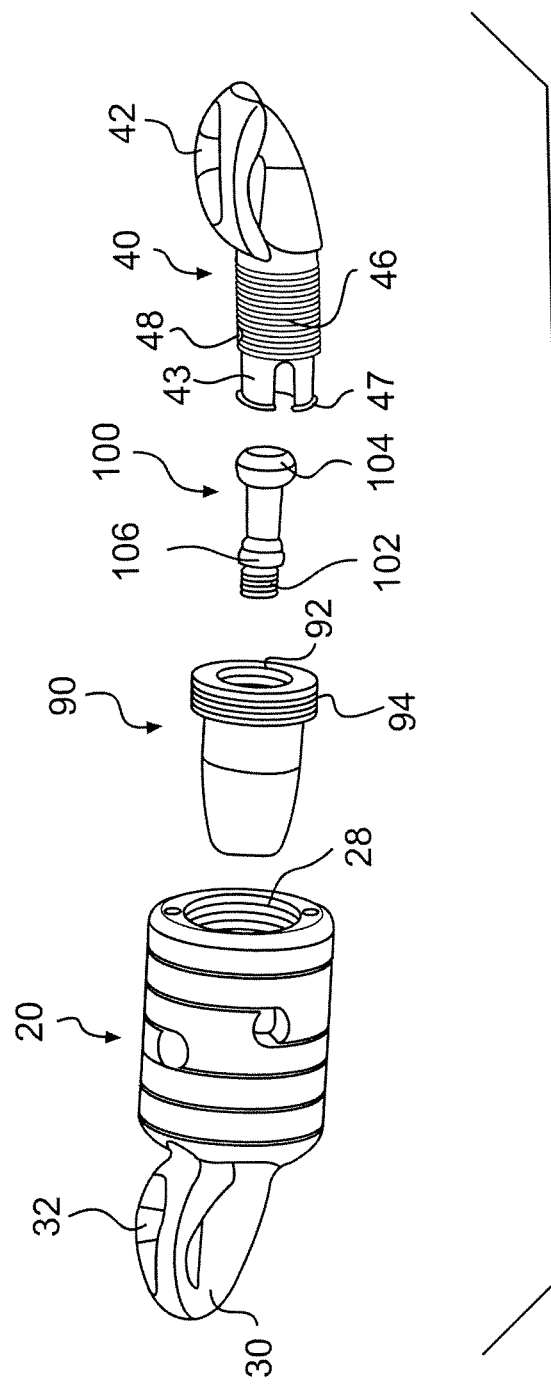
FIG. 6 illustrates an exploded view of the flexible coupler of FIGS. 4B-4C.

Each gripping arm 30, 40 of the coupler 20 can include, on one side, a concavely-shaped cavity 34, 44 configured to seat against a semi-spherical ball bearing 60, shown in FIGS. 5A-5B, and 6. The ball bearing 60 can have a through-hole, allowing it to fit over the bone anchor 50. In one embodiment, the bone anchor 50 may have an elongate, threaded shaft 52 extending into a flange 56 that connects to a head portion 54 upon which the ball bearing 60 may be placed. The flange 56 may further include serrations 57 to facilitate anchorage to bone tissue and reduce loosening of the anchor 50 over time. The bone anchor 50 may be, for example, a pedicle screw. Preferably, the bone anchor 50 can be cannulated to enable the unit 10 or system 8 to be percutaneously delivered. The concavely-shaped cavities 34, 44 allow the gripping arms to slide or rotate with respect to the bearing 60, thereby enabling the gripping arms 30, 40 to move relative to the bone anchor 50. Other appropriate structures may be used to connect the flexible body 22 to the bone anchors 50 while permitting relative movement between the two.

Figure 10:
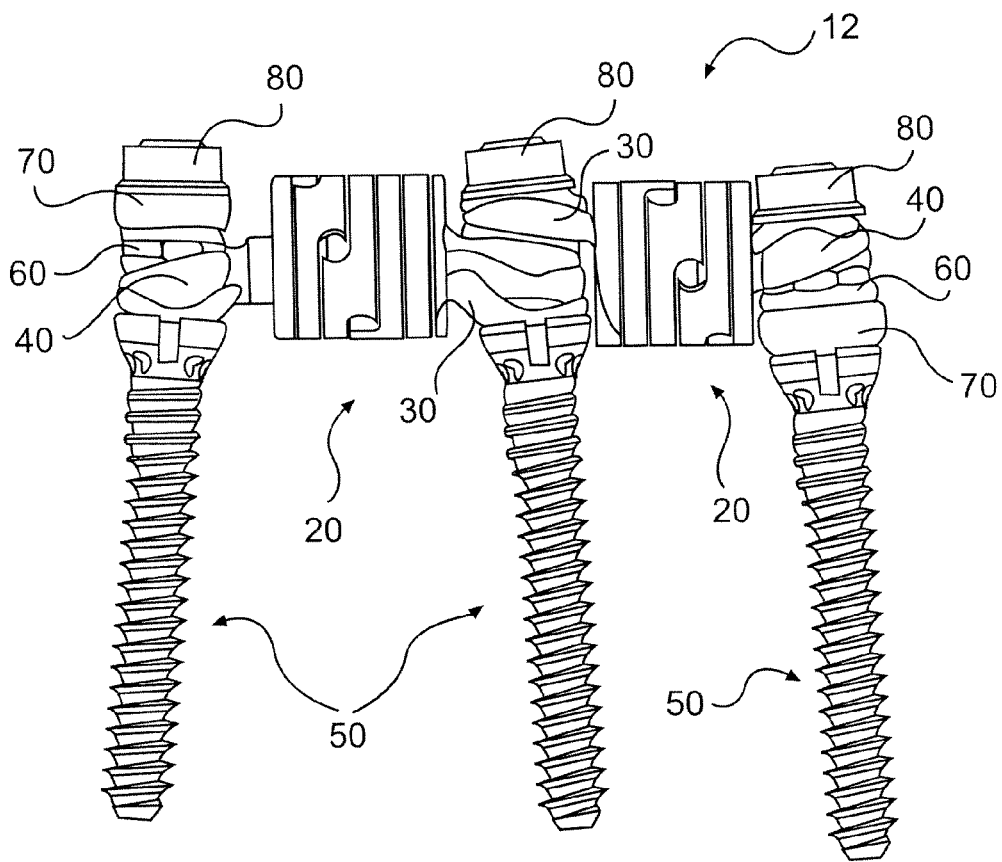
FIG. 10 illustrates a side view of a portion of the system of FIGS. 9A-9B.

As further shown in FIGS. 5A, 5B and 10, a washer 70 may be placed onto the screw 50 and against the flange 56 or nut 80. The washer 70 can be configured and shaped to lie against the ball bearing 60. An assembled functionally dynamic stabilization unit 10 would further include a nut 80 screwed onto the head portion 54 of the screw 50 to secure the components to one another, as illustrated in FIGS. 4A and 5A.

Each functionally dynamic stabilization unit 10 is configured to allow a range of motion or displacement of between 1.5 and 3.0 mm, where displacement may be measured from the center of a first pedicle screw connected to a first gripping arm 30 to the center of a second pedicle screw connected to the second gripping arm 40. This displacement or range of motion may be achieved, for example, through rotation, extension, or translation.

FIG. 6 illustrates an exploded view of the flexible coupler of FIGS. 4A-4C. As shown, in some embodiments, one of the gripping arms 40 may be removably attached to the coupler 20. In one embodiment, the coupler 20 can include a threaded opening 28 for securing the second gripping arm 40, and other components, to the coupler 20. Within the flexible coupler 20, there may be a sleeve 90 having an opening 92 at one end and including a threaded rim 94 around the opening 92 for threadably connecting to the coupler body 22. The sleeve 90 can be configured to reside within the coupler body 22 and to receive and cooperate with a pin 100. The pin 100 can comprise an elongate body 102 with a threaded end, the body 102 extending into a semispherical head region 104 and including a skirt or shoulder region 106. Collectively, the sleeve 90 and pin 100 form an extension and compression stop within the coupler body 22, functioning to limit range of motion of the flexible coupler 20 to the patient's neutral or active zone.

Figure 8A:
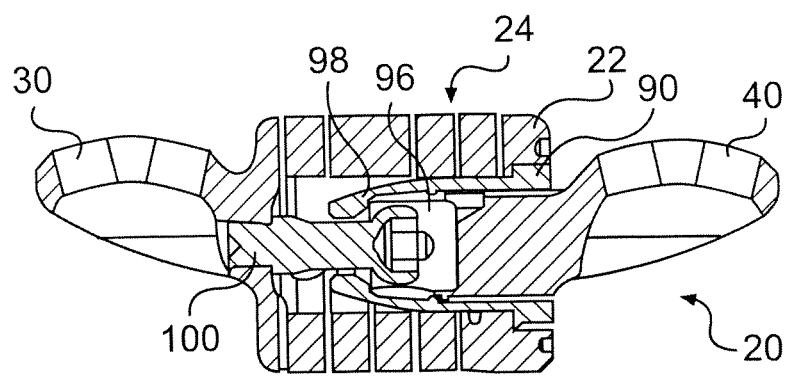
FIG. 8A illustrates a cross-sectional view of the flexible coupler of FIG. 4B in a resting state.
Figure 8B:
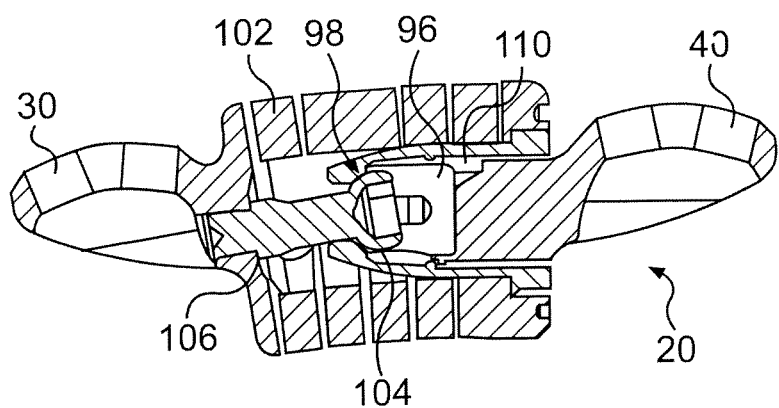
FIG. 8B illustrates a cross-sectional view of the flexible coupler of FIG. 4B in a fully expanded state.
Figure 8C:
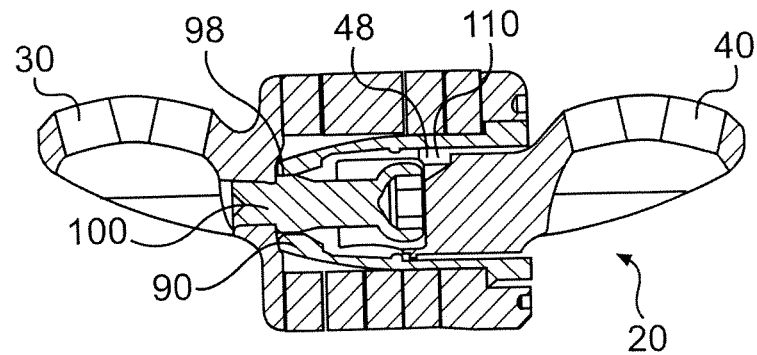
FIG. 8C illustrates a cross-sectional view of the flexible coupler of FIG. 4B in a fully compressed state.
Figure 8D:
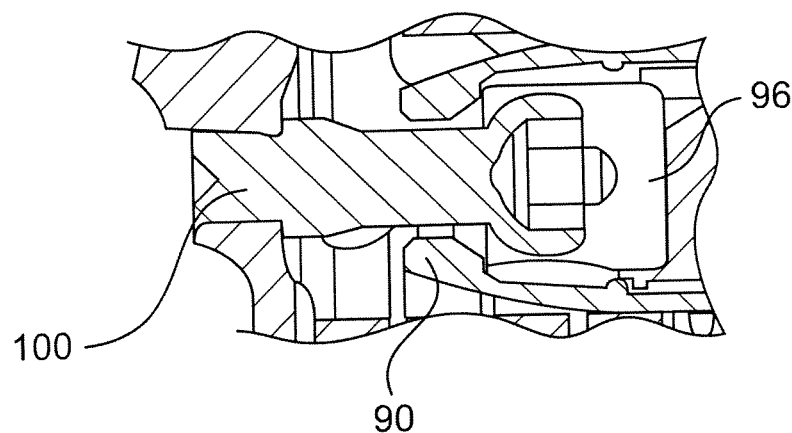
FIG. 8D illustrates an enlarged view of a portion of the flexible coupler of FIG. 8A in a resting state.

The rim 92 of the sleeve 90 may be threaded to engage the threaded end 46 of the detachable second gripping arm 40. The overall length of the coupler 20 may be adjusted by varying the amount of threading of the second gripping arm 40 into the sleeve 90 (i.e., varying the number of rotations of the arm 40 into the sleeve 90). As shown, the threaded end 46 of the detachable second gripping arm 40 may extend into a plurality of compressible finger projections 43, each projection 43 terminating at a flanged lip 47. The flanged lip 47 serves as a locking mechanism, preventing the second gripping arm 40 from being unscrewed from the sleeve 90 after assembly. The threaded end 46 may also include a well 48 for receiving an elastomeric plug 110, as shown in FIG. 8C. The elastomeric plug 110 may be formed of a soft, compliant plastic material such as, for example, silicone, polyethylene, or polyethyletherketone (PEEK). As the second detachable gripping arm 40 is threaded onto the sleeve 90, the plug 110 interacts with the threaded opening 92, reducing the slack or play between the arm 40 and the sleeve 90. Other suitable structures that permit adjustment of the length of the flexible body while providing control of the amount of compression and extension of the flexible body may also be used. For example, a gripping arm can be attached at a friction fit, a telescoping connection, or using a ratchet mechanism.

Figure 7A:
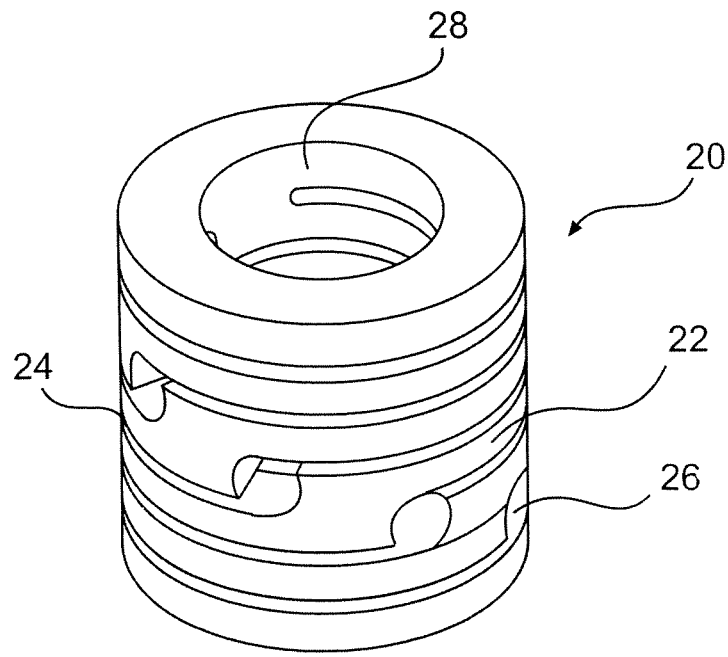
FIG. 7A illustrates a perspective view of a portion of the flexible coupler of FIGS. 4B and 4C.
Figure 7B:
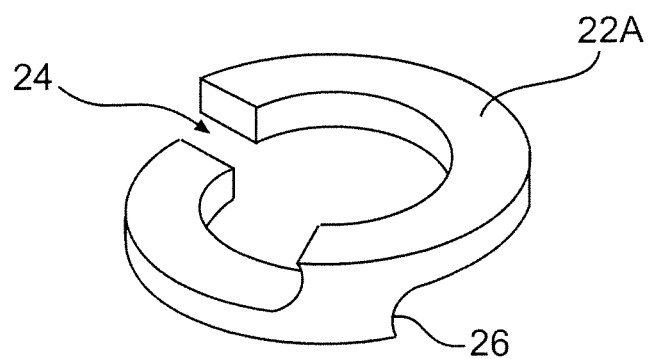
FIG. 7B illustrates a perspective view of a section of the portion of the flexible coupler of FIG. 7A.

As shown in detail in FIGS. 7A and 7B, in one exemplary embodiment, the coupler body 22 may include a cylindrical body comprised of a series of coil units 22A. The series of coil units 22, when connected to one another to form a stepwise series of slots 24, whereby each slot 24 terminates at an opening 26 of the flexible body 22. In some embodiments, the series of coil units 22A can be formed from a single piece of material such that the units 22A are integrally connected with one another. For example, in one embodiment, the coil units 22A can be etched or cut from a single, tubular piece of material. In other embodiments, one or more coil units 22A can be formed individually and stacked upon one another. The stacked coil units 22A can be connected to one another, for example, by welding or through mechanical connections.

It is contemplated that the coupler body 22 may vary in degree of stiffness based on the height, width, distance or angle between two adjacent slots 24 and the number of units 22A forming the coupler body 22. Further, one or more units 22A may be formed from different materials so as to vary the mechanical properties of the body 22. In addition, the dimensions of the units 22A, slots 24, and openings 26 can be varied within a single body 22.

FIGS. 8A-8D show an embodiment of the fully assembled flexible coupler 20 in a resting state (FIGS. 8A and 8D), fully-expanded or distracted state (FIG. 8B), and a fully compressed state (FIG. 8C). In the resting state, shown in FIG. 8A and an expanded view in FIG. 8D, the pin 100 and sleeve 90 are not engaged (i.e., free of resistive forces or encumbrances). In the fully-expanded or distracted state (FIG. 8B), the pin head 104, having a dimension that is larger than the width of the narrowed opening 98, abuts the narrowed opening 98 of the sleeve 90, preventing the flexible coupler body 22 from over expanding. In the fully-compressed state (FIG. 8C), the end of the sleeve 90 with the narrowed opening 98 abuts the inner edge of the first gripping arm 30, as shown. The cooperation of the sleeve 90 and pin 100 inside the coupler body 22 provides a distraction-compression stopping mechanism to control or limit the range of motion that can be offered, preventing not only injury or damage to the affected vertebral segments but also to the functionally dynamic stabilization unit itself. Other types of cooperating elements, such as, for example, a telescoping element or internal piston, may be sued to control or limit the range of motion of the coupler body 22.

Figure 9A:
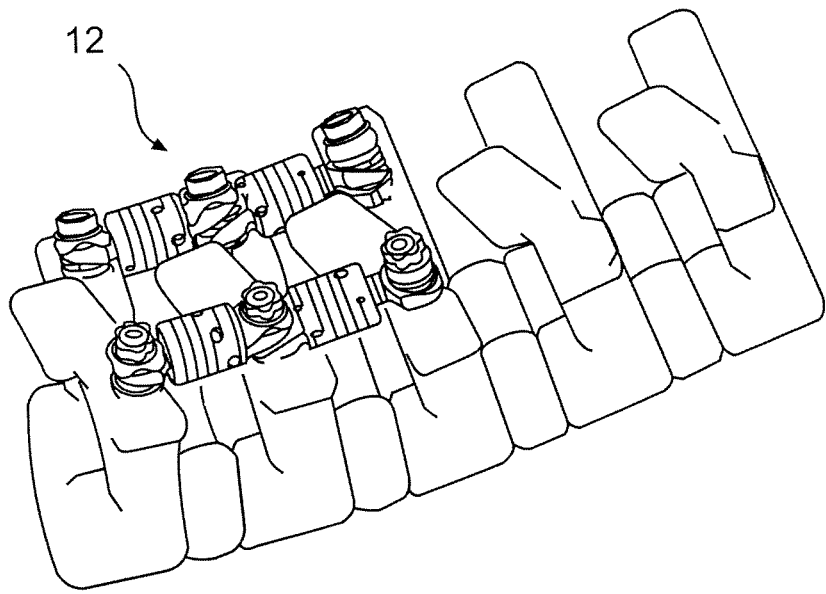
FIG. 9A illustrates a perspective view of another embodiment of an implanted functionally dynamic stabilization system.
Figure 9B:
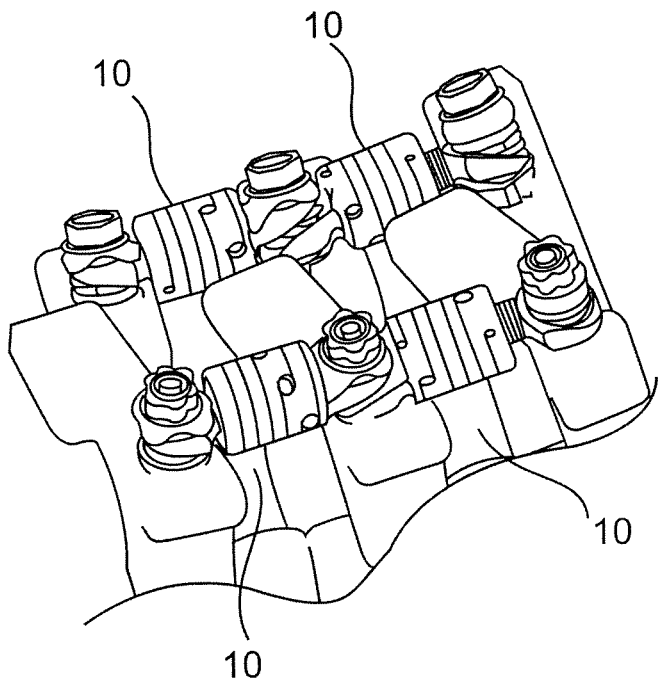
FIG. 9B illustrates an enlarged view of the implanted system of FIG. 9A.

As previously mentioned, the functionally dynamic stabilization unit 10 may be used alone to stabilize a pair of vertebral segments. Further, if desired, more than one unit 10 may be used in combination to form a multi-level, functionally dynamic stabilization system 12, as shown in FIGS. 9A and 9B. The multi-level, functionally dynamic stabilization system 12 may include two or more of the units 10 connected to one another.

FIG. 10 illustrates a side view of the system shown in FIGS. 9A-9B. As shown, the system 12 includes a pair of flexible couplers 20 connected in series. The couplers 20 are positioned such that the first gripping arm 30 of each coupler 20 is placed around one ball bearing 60, with a bone anchor 50 and nut 80 securing the combination together. It is understood that more than two couplers 20 may be connected in this manner, and either the first 30 or second 40 gripping arm of any single coupler may be combined with the first 30 or second 40 gripping arm of another coupler 20 on a bone anchor 50. Any number of couplers 20 may be implanted either along one side, or on both sides, of a patient's spine. Further, the units 10 may have differing mechanical properties according to the patient's pathology and anatomy.

Figure 11A:
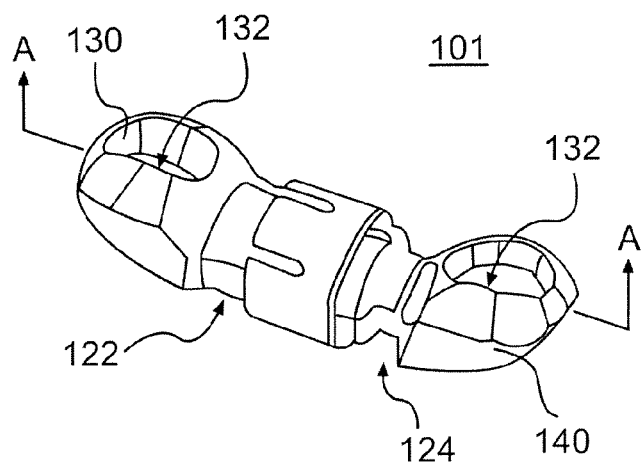
FIG. 11A illustrates a perspective view of a rigid coupler that may be used with the stabilization systems of the present disclosure.

In some embodiments, the stabilization systems of the present disclosure can allow fusion of one or more vertebral motion segments, along with functionally dynamic stabilization of other motion segments. To this end, the stabilization system may include a rigid, fusion-promoting coupler 101, such as the one shown in FIG. 11A. The rigid coupler 101 can be configured for use with the bone anchors 50, ball bearings 60, and washers 70 described previously. As illustrated, the rigid coupler 101 comprises two components 122, 124, each of which extends to a gripping arm 130, 140, respectively, in a manner similar to that in the flexible coupler 20 previously described. Each of the arms 130,140 includes an opening 132 for attachment to a bone anchor 50, in a manner similar to that described with respect to the flexible coupler 20.

Figure 11B:
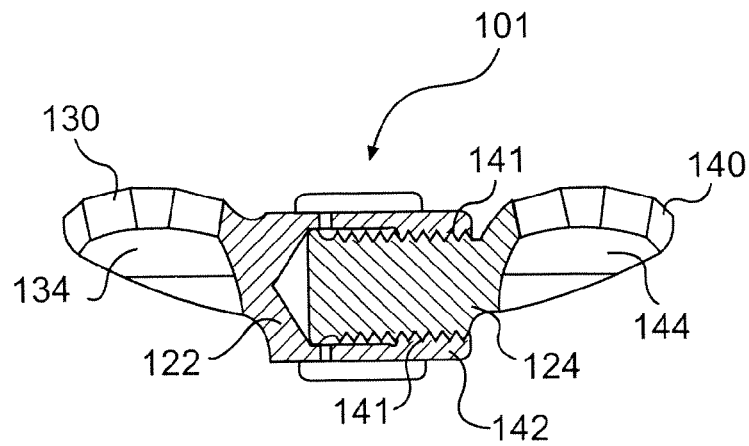
FIG. 11B illustrates a cross-sectional view of the rigid coupler of FIG. 11A, taken along line A-A.

As further shown in FIG. 11B, the two components 122, 124 may be attached to one another to allow adjustment of the length of the rigid coupler 101. For example, the components 122, 124 can include threaded surfaces, and the length of the rigid coupler 101 can be adjusted by twisting one component 122 with respect to the other component 124, much like the manner previously described for adjusting the length of the flexible coupler 20. Each of the gripping arms 130, 140 can also include, on an underside, a concave cavity 134, 144, respectively, configured to seat against a semi-spherical ball bearing 60. Hence, the implantation of the rigid coupler 101 to the bone anchors 50 is similar to that for the flexible coupler 20, as previously described.

Figure 11C:
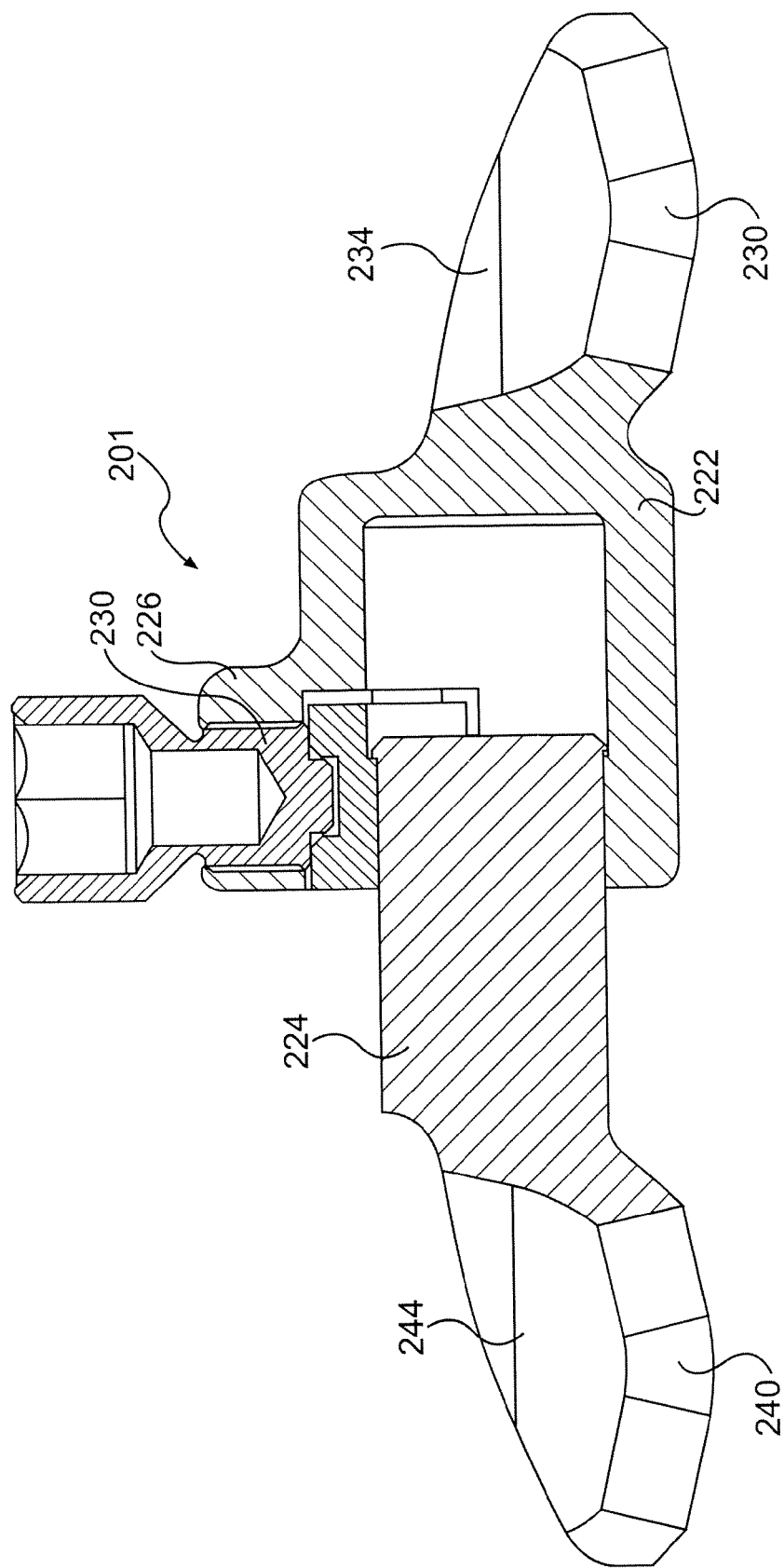
FIG. 11C illustrates a side cross-sectional view of an alternative embodiment of a rigid coupler that may be used with the stabilization systems of the present disclosure.

As shown in FIG. 11C, an alternative embodiment of a rigid, fusion-promoting coupler 201 may be provided. The rigid, fusion-promoting coupler 201 is similar to rigid coupler 101 except that it may not utilize threaded surfaces of components for adjusting a length of the coupler 201. The rigid coupler 201 can be configured for use with the bone anchors 50, ball bearings 60, and washers 70 described previously. As illustrated, the rigid coupler 201 comprises two components 222, 224, each of which extends to a gripping arm 230, 240, respectively, in a manner similar to that in the flexible coupler 20 previously described. Each of the arms 230, 240 includes an opening (not shown) for attachment to a bone anchor 50, in a manner similar to that described with respect to the flexible coupler 20. Each of the gripping arms 230, 240 can also include, on an underside, a concave cavity 234, 244, respectively, configured to seat against a semi-spherical ball bearing 60.

The first component 222 and the second component 224 may be movable relative to one another to facilitate adjustment of the length of the coupler 201. Instead of threaded surfaces, the component 222 may include a cavity 226 configured to receive a fastening element 230 to secure the first component 222 relative to the second component 224. Because the first and second components do not include threaded surfaces, they may be moved relative to one another by sliding the components rather than twisting. Such an embodiment permits the surgeon to adjust the length of the rigid coupler 201 in situ as necessary.

The fastening element 230 may be any suitable fastening element such as a screw or a nut. For example, the fastening element 230 may comprise a break-away nut having a first portion configured to fixingly engage the portion 226 of component 222 to fix the position of the first component 222 relative to the second component and a second portion configured to engage an insertion tool for tightening of the first portion to the rigid coupler. The second portion of the break-away nut may be a break-away portion that has a thinner wall or area of lower yield-strength material, and is configured to break when a sufficient torque is applied (i.e., when the nut 230 has been sufficiently tightened). An internal surface of cavity 226 and an external surface of the fastening element 230 may be provided with threads to facilitate engagement of the cavity 226 with the fastening element 230.

As noted, the stabilization system may include both functionally dynamic, flexible couplers 20 and rigid couplers 101, thereby providing a modular system that allows the combination of motion preservation and fusion at discrete segments of the patient's spine. By permitting interchangeability of the rigid coupler 101 and a flexible coupler 20, in the system, the surgeon will have greater flexibility to address the specific needs of the patient. Therefore, one spinal segment may have functionally dynamic stabilization (i.e., non-fusion), while an adjacent segment may have rigid, segmental fixation (i.e., fusion).

Figure 12:
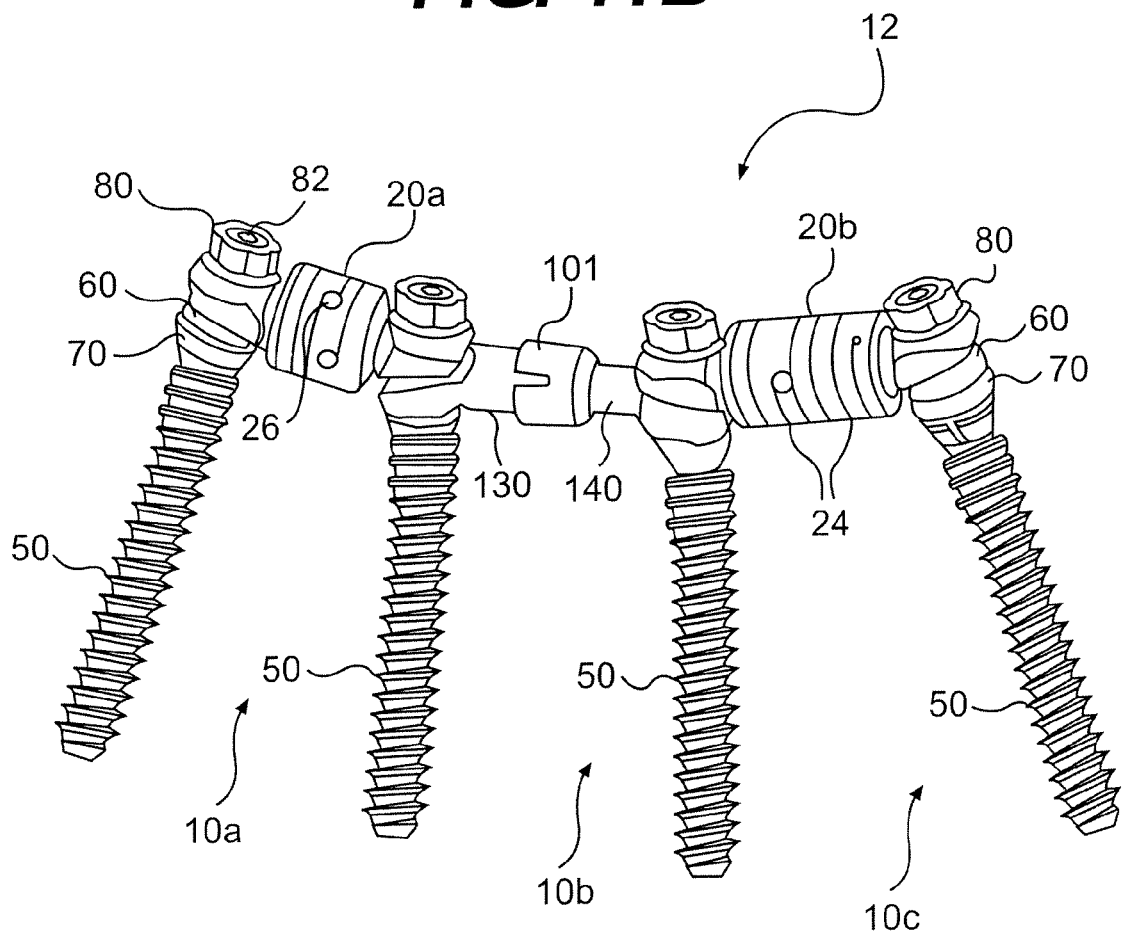
FIG. 12 illustrates a perspective view of a modular, multi-segmental stabilization system, according to another embodiment of the disclosure.

FIG. 12 illustrates a multi-segmental system 12 comprising three discreet stabilization units 10a, 10b, 10c utilizing flexible couplers 20a, 20b and a rigid coupler 101. The flexible couplers 20a, 20b of units 10a and 10c increase the segmental stiffness of the affected motion segment and restrict the range of motion in flexion, extension, lateral bending and rotation, while preserving motion. By selecting an appropriately-sized coupler 20a, 20b, the posterior segmental height can be adjusted as well. In addition, the rigid, fusion-promoting coupler 101 of unit 10b provides rigid, segmental fixation, thereby promoting fusion, while utilizing the same type of bone anchors 50 and instruments.

The modular system 12 provides a number of advantages. For example, initially, an implanted system may include only functionally dynamic, flexible couplers 20 connected to vertebra with bone anchors 50, as described above. However, subsequently, due to progression in disease, unabated pain, other symptoms, or other changes in a patient's condition, it may be desirable to fuse one or more previously-treated levels. Therefore, in subsequent surgeries, a surgeon can simply replace a previously-implanted flexible coupler with a rigid coupler 101, while likely using the same bone anchors.

As noted previously, the units and systems of the present disclosure can be implanted using a minimally-invasive, muscle-sparing approach. Such approaches can include percutaneous methods or a series of small incisions that minimize tissue damage.

Figure 13:
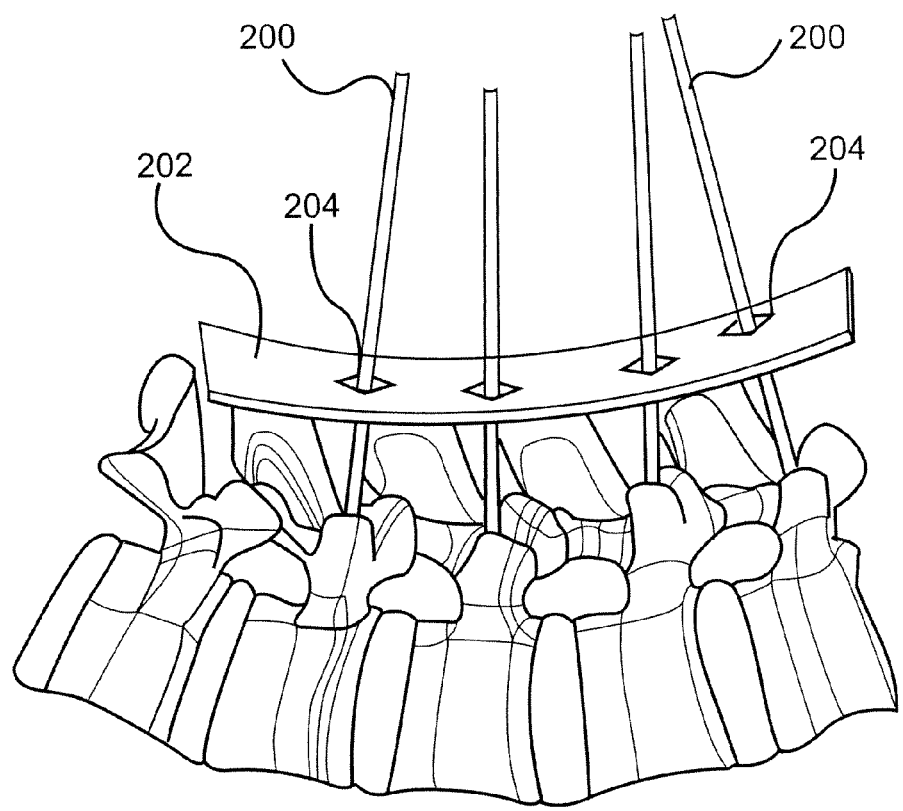
FIG. 13 illustrates a perspective view of a wire template and K-wires used to facilitate implantation of the spinal stabilization systems of the present disclosure.

FIGS. 13-19 illustrate exemplary embodiments of insertion instruments that may be provided separately or as a set along with the system. In one exemplary method of the present system, a series of K-wires 200 are inserted into the pedicles of the patient's spine. The K-wires 200 may be inserted through a series of small incisions in the patient's back. Further, as shown in FIG. 13, a wire template 202 may be provided to assist the surgeon in placement of the incisions and K-wires 200. The wire template 202 may include predetermined openings 204 that align with the pedicles of the patient's spine, as illustrated. The openings 204 may be bilaterally located in line with both pedicles of vertebrae to be treated. The template may be provided in various sizes to accommodate patients having variations in pedicle spacing.

Figure 14A:
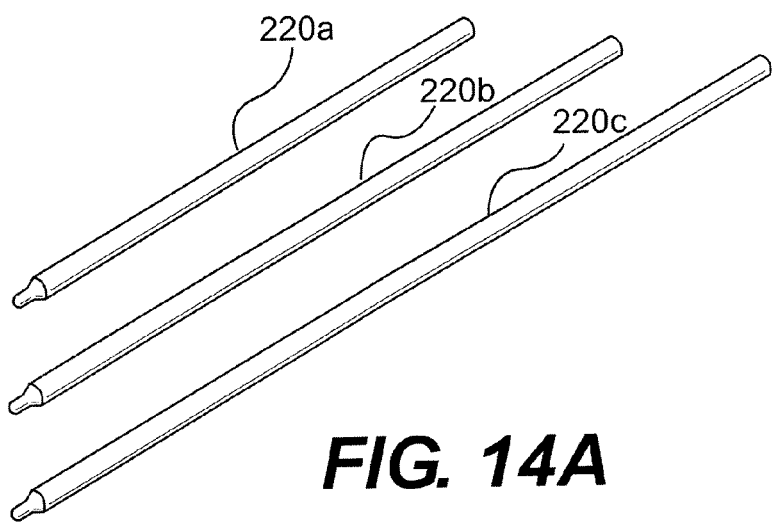
FIG. 14A illustrates a perspective view of a set of extension rods used to facilitate implantation of bone anchors using the methods of the present disclosure.
Figure 14B:
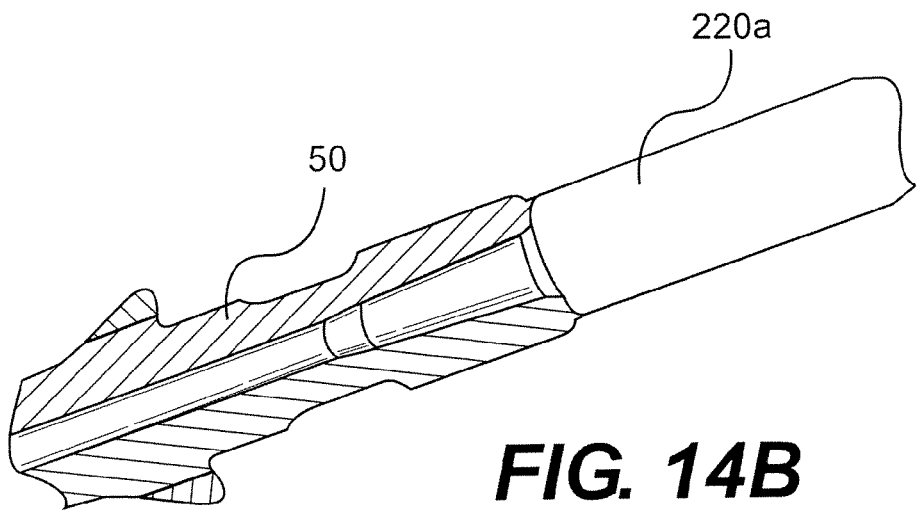
FIG. 14B illustrates a partial cutaway view of one of the extension rods of FIG. 14A connected to a bone anchor.

After insertion of the K-wires 200, the cannulated bone anchors 50 may be passed over the K-wires 200, and using a series of extension rods 220a, 220b, 220c, shown in FIG. 14A, the bone anchors can be implanted within selected vertebra. As shown in FIG. 14B, the extension rods can attach to the head portions 54 of the bone anchors 50 to allow manipulation of the anchors 50. In addition, a dilatation sleeve (not shown) can be provided, and the extension rods can be passed through the dilation sleeve to access the implantation site. After or during implantation of the bone anchors 50, the extension rods 220 can be used to manipulate the anchors 50 and the attached vertebrae to ascertain the full range of motion in a static condition and with an applied load. Such information may be useful to the surgeon to predict the possible range of corrective motion desirable for that spine segment.

Figure 15:
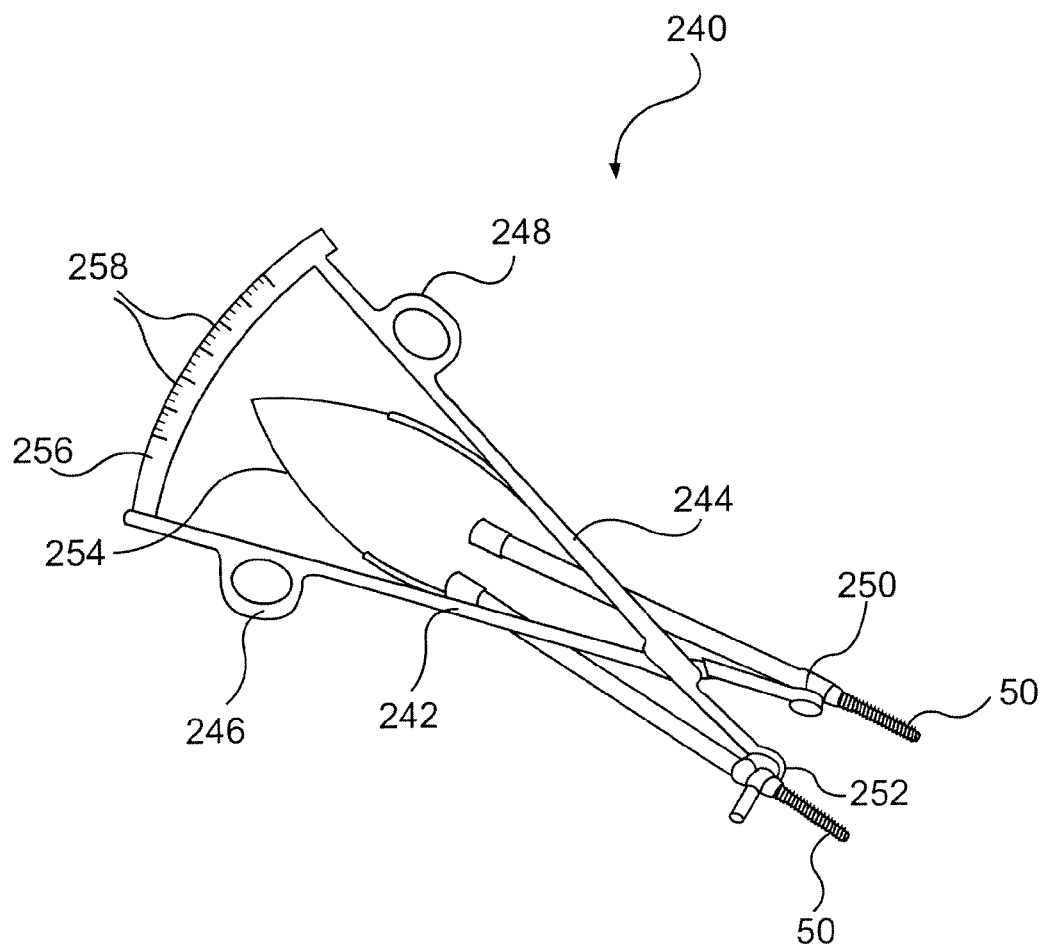
FIG. 15 illustrates a perspective view of a caliper.

A caliper 240, as illustrated in FIG. 15, may also be provided with the instrument set. The caliper 240 can comprise a pair of pivoting arms 242, 244, each arm extending to a finger engaging opening 246, 248, respectively, and terminating at an opposite end into a gripping end 250, 252, respectively. The pivoting arms 242, 244 can be connected via a leaf spring 254. As shown, the ends of the arms 242, 244 are configured to provide a reading or measurement of the distance between a pair of adjacent bone anchors 50 using the indicia markings 258 on a backboard 256. The gripping ends 250, 252 can be configured to hold a portion of the ball bearing 60 of each bone anchor 50. This enables the caliper 240 to function even when the bone anchors 50 are situated in a nonparallel or unique angle relative to one another.

Figure 16:
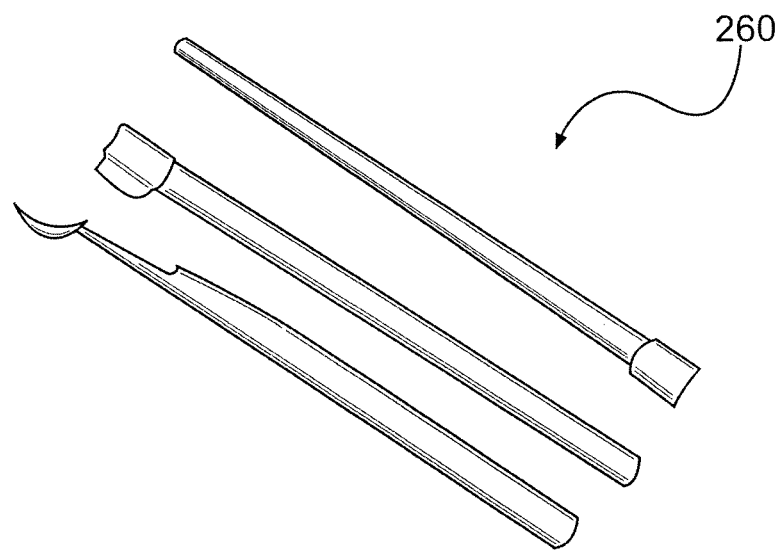
FIG. 16 illustrates a perspective view of an alternative set of extension rods according to the present disclosure.
Figure 17:
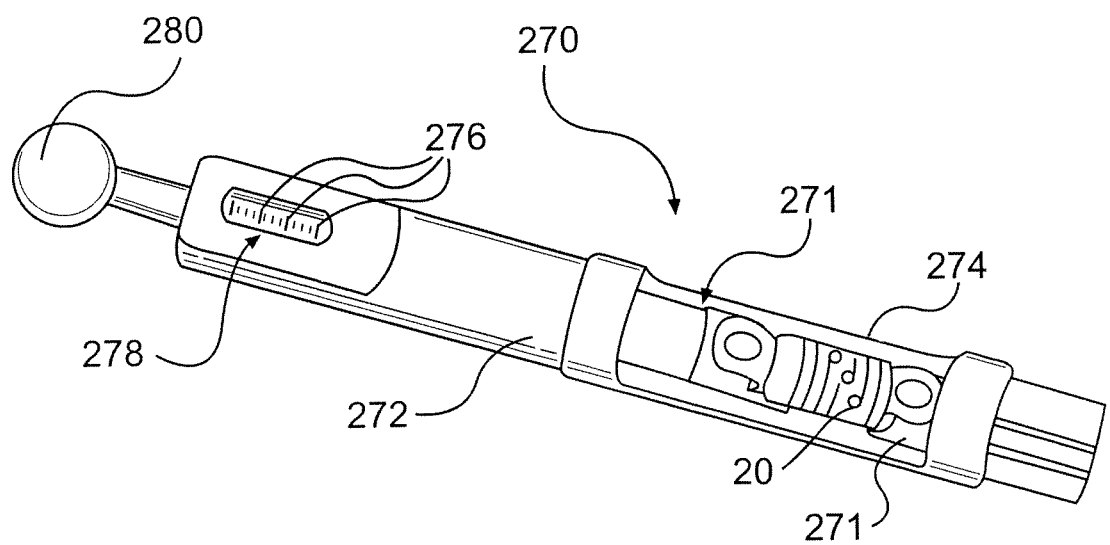
FIG. 17 illustrates a perspective view of an instrument for adjusting the length of a flexible coupler.

FIG. 16 illustrates various rod extensions 260 that are configured to connect to other components of the anchor, such as the ball bearing 60, washer 70, or nut 80. Each of these rod extensions 260 enables minimally-invasive or percutaneous manipulation of the respective component.

Once the bone anchors 50 are in place and the distance between a pair of adjacent bone anchors 50 has been determined, a surgeon may then select a suitably-sized functionally dynamic, flexible coupler 20 or a rigid, fusion-promoting coupler 101 for placement between the anchors 50. A coupler length adjuster 270, similar to the one shown in FIG. 17, may be provided to ensure that the coupler length is correct prior to insertion. As illustrated, the length adjuster 270 may include a body 272 having a pair of grips 271, between which a coupler 20, 101 can be held. The pair of grips 271 form the insertion area 274 for the coupler. Within the body 272 is a spring-loaded mechanism that exerts biased force against one of the grips 271. The spring-loaded mechanism may be controlled by turning a knob 280, thereby twisting the coupler 20,101, and consequently adjusting its length. The body 272 may further include a window 278 within which there appear indicia 276 indicating the length of the coupler. Although a flexible coupler 20 is illustrated, it is understood that the length adjuster 270 is also applicable for use with a rigid coupler 101.

Figure 18A:
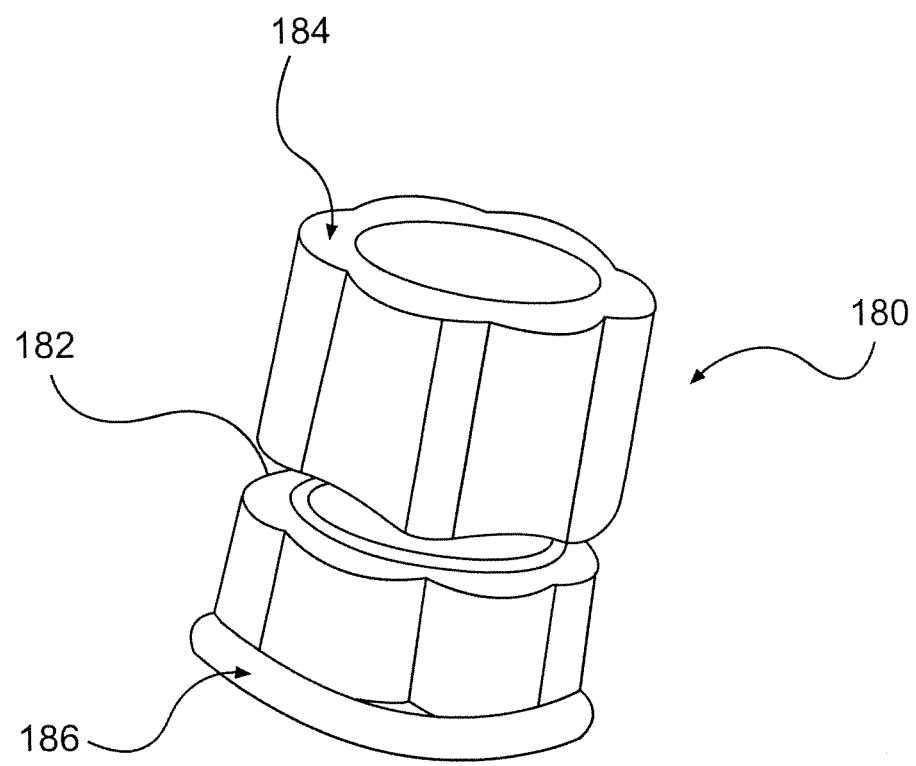
FIG. 18A illustrates a perspective view of a nut that may be used to secure stabilization units of the present disclosure.

The appropriately-sized coupler 20, 101 is then slid down the K-wires 200 and onto the ball bearings 60 of the bone anchors 50. Subsequently, nuts 80 may be used to secure the coupler 20, 101 in place. In some embodiments, the nuts 80 may have features that prevent over- or under tightening. For example, FIG. 18A illustrates an exemplary embodiment of a suitable nut 180 having a break-away portion 182, connecting an anchor-engaging lower portion 186 to an upper portion 184. The break-away portion 182, having a thinner wall or area of lower yield-strength material, is configured to break when a sufficient torque is applied (i.e., when the nut 180 has been sufficiently tightened).

Figure 18B:
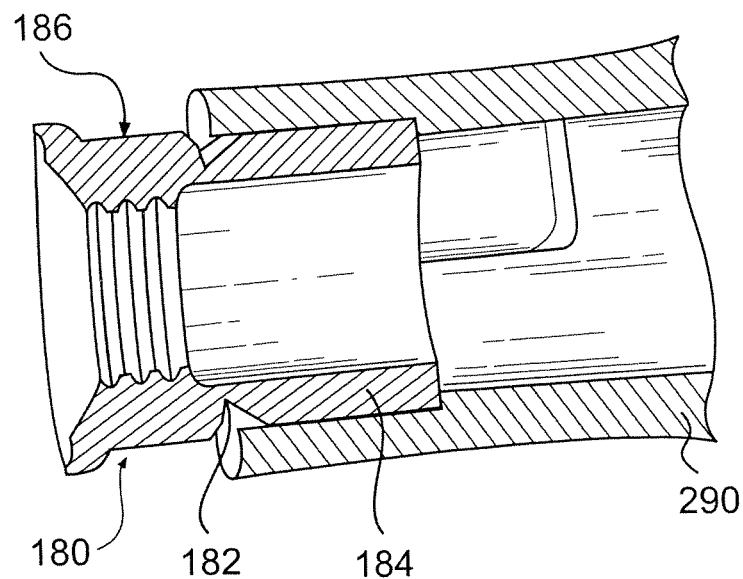
FIG. 18B illustrates a partial cutaway view of the nut of FIG. 18B coupled to the insertion tool of FIG. 19.
Figure 19:
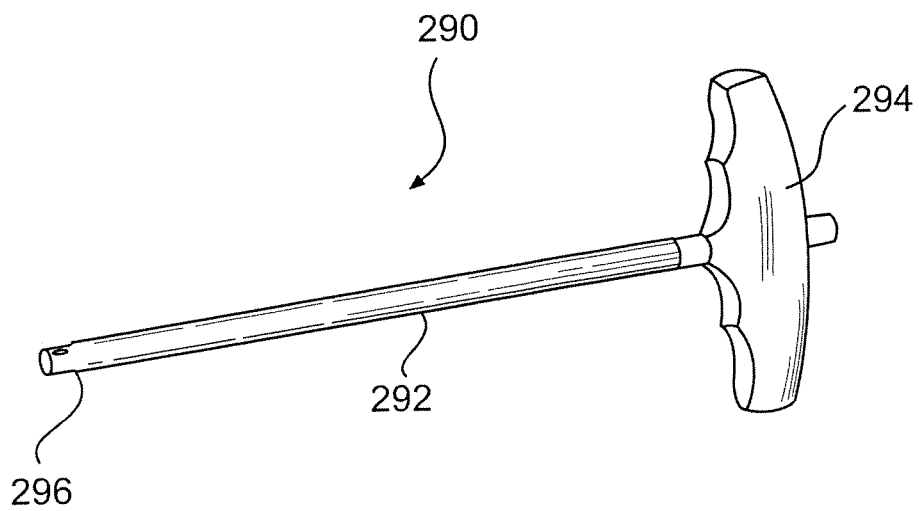
FIG. 19 illustrates a perspective view of an insertion tool.

The nut 180 can be inserted through the minimally-invasive approach used to implant the bone anchors 50 and couplers 20, 101. For example, FIG. 19 shows an exemplary insertion tool 290 useful for insertion of the nut 180. The insertion tool 290 comprises an elongate body 292 extending from a handle portion 294 to a nut coupling end 296 at an opposite end. The coupling end 296 may be configured to securely attach to the nut at the upper portion 184, as shown in FIG. 18B, and the elongate body 292, with a nut coupled thereto, can be inserted into a previously defined access site to secure the nut 180 to a bone anchor 50. With sufficient tightening, the nut 180 will break at break-away portion 182, leaving the lower portion 186 on a bone anchor and allowing the upper portion 184 to be withdrawn.

The surgeon may elect to repeat this process at an adjacent level until all the affected levels of the patient's spine have been treated. The entire process may be done percutaneously and/or with minimal disruption to the surrounding tissue.

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

The invention claimed is:

1. A modular spinal stabilization system, comprising:
   a flexible coupler including a flexible body, a pair of arms, the arms being located at opposed ends of the flexible coupler, and a range-of-motion limiting mechanism configured to control an amount of bending, an amount of compression, and an amount of extension of the flexible coupler, the range-of-motion limiting mechanism comprising an attachable sleeve with a narrowed distal opening residing within the flexible body and a pin comprising an elongated body with an enlarged head region and shoulder region, the pin being configured to be received within and cooperate with the attachable sleeve to form an extension and compression stop within the flexible body, the sleeve extending internally from a first end of the flexible coupler towards a second end of the flexible coupler, and the elongated body of the pin extending internally from the second end of the flexible coupler towards the first end of the flexible coupler, the enlarged head region of the pin being disposed within the sleeve and dimensioned such that the enlarged head region abuts the wall of the narrowed distal opening when the flexible coupler is elongated or bent, and the sleeve abuts the second end of the flexible coupler when the flexible coupler is compressed, wherein at least one of the arms has an adjustable connection to the flexible body that permits relative movement of the arm to the flexible body in order to adjust the overall length of the flexible coupler;
   a rigid coupler including a pair of arms, the arms being located at opposed ends of the rigid coupler; and
   a fixation system including a plurality of bone anchors configured to cooperate with the arms of the flexible and rigid couplers to attach the couplers to bone.

2. The system of claim 1, wherein the flexible body comprises a cylindrical body portion including one or more slots in a wall of the cylindrical body portion.

3. The system of claim 1, wherein the flexible body is extendable and compressible along a longitudinal axis of the flexible body.

4. The system of claim 1, wherein the flexible body is bendable relative to a longitudinal axis of the flexible body.

5. The system of claim 1, wherein at least one of the flexible coupler arms is attached to the flexible coupler at a threaded connection.

6. The system of claim 1, wherein an arm of the flexible coupler is attached to the flexible coupler at a threaded connection, and the length of the flexible coupler is adjustable through rotation of the arm with respect to the flexible coupler.

7. The system of claim 1, wherein the pin is cooperatively and movably positioned within the sleeve, such that movement of the pin relative to the sleeve in a first direction defines a range of extension of the flexible coupler, and movement of the pin relative to the sleeve in a second direction, opposite to the first direction, defines a range of compression of the flexible coupler.

8. The system of claim 1, wherein the fixation system further includes a plurality of ball bearings and a plurality of nuts.

9. The system of claim 8, wherein the flexible coupler is configured to be movable relative to the plurality of bone anchors.

10. The system of claim 8, wherein the flexible coupler is configured to be movable relative to the fixation system.

11. The system of claim 1, wherein the rigid coupler is adjustable in length.

12. The system of claim 11, wherein an arm of the rigid coupler is attached to the rigid coupler at a threaded connection, and the length of the rigid coupler is adjustable through rotation of the arm with respect to the rigid coupler.

13. The system of claim 1, wherein the fixation system further includes a plurality of semi-spherical ball bearings, and wherein the arms of the flexible coupler and the arms of the rigid coupler each include a concave portion having an opening configured to engage a semispherical ball bearing.

14. The system of claim 1, wherein the fixation system further includes a plurality of nuts for securing the rigid coupler or flexible coupler to a respective bone anchor, each nut having a narrowed break-away portion configured to break when sufficient torque is applied to the nut.

15. The system of claim 1, further comprising a second flexible coupler.

16. The system of claim 1, further comprising a second rigid coupler.

17. The system of claim 1, further comprising a second flexible coupler and a second rigid coupler.

18. A method of treating a spine, comprising:
attaching a first bone anchor to a first vertebra;
attaching a second bone anchor to a second vertebra adjacent the first vertebrae;
providing a flexible coupler having a flexible body portion, a pair of arms located at opposed ends of the coupler, and a range-of-motion limiting mechanism configured to control an amount of bending, an amount of compression, and an amount of extension of the coupler, the range-of-limiting mechanism comprising an attachable sleeve having a narrowed opening residing within the flexible body portion and a pin comprising an elongated body with an enlarged head region and shoulder region, the pin being configured to be received within and cooperate with the attachable sleeve to form an extension and compression stop within the flexible body portion, wherein at least one of the flexible coupler arms has an adjustable connection to the flexible body that permits relative movement of the flexible coupler arm to the flexible body in order to adjust the overall length of the flexible coupler;
adjusting a length of the flexible coupler by rotating one of the flexible coupler arms relative to the body portion to adjust an amount that the arm extends from the body portion prior to attaching the flexible coupler to the bone anchors; and
connecting first and second arms of the flexible coupler to the first and second bone anchors, respectively.

19. The method of claim 18, further including attaching a third bone anchor to a third vertebra; and
attaching a rigid coupler to the third bone anchor and one of either the first bone anchor or second bone anchor, wherein the rigid coupler is configured to prevent movement between two of the vertebrae.

20. The method of claim 19, further including adjusting a length of the rigid coupler prior to attaching the rigid coupler to the bone anchors.

21. The method of claim 20, wherein adjusting the length of the rigid coupler includes rotating an arm of the rigid coupler to adjust an amount that the rigid coupler arm extends from the rigid coupler.

22. The method of claim 18, further including disconnecting the flexible coupler from the first and second bone anchors attached to the first and second vertebrae; and
replacing the flexible coupler with a rigid coupler.

23. The method of claim 22, wherein replacing the flexible coupler includes connecting the rigid coupler to the first and second bone anchors attached to the first and second vertebrae.

24. The method of claim 18, wherein the range-of-motion limiting mechanism is an internal range-of-motion limiting mechanism configured to limit motion of the flexible body portion in bending, compression, and expansion.

25. The method of claim 24, wherein the sleeve extends from a first end of the flexible coupler towards a second end of the flexible coupler and the narrowed opening is a narrowed distal opening, and the elongated body of the pin extends from the second flexible coupler, and further comprising controlling an amount of expansion and an amount of bending of the flexible coupler by positioning the pin within the sleeve such that the enlarged head region abuts the wall of the narrowed distal opening when the flexible coupler is elongated or bent.

26. The method of claim 24, wherein the sleeve extends internally from a first end of the flexible coupler towards a second end of the flexible coupler and the narrowed opening is a narrowed distal opening, and the elongated body of the pin extends from the second flexible coupler, and further comprising controlling an amount of compression of the flexible coupler by positioning the pin within the sleeve such that the sleeve abuts the second end of the flexible coupler when the flexible coupler is compressed.

* * * * *